United States Patent

Hassard et al.

[11] Patent Number: 6,017,435
[45] Date of Patent: Jan. 25, 2000

[54] MOLECULAR IMAGING

[75] Inventors: John Francis Hassard, Princess Gardens; Stuart Hassard, Cambridge; Alison Mary Mainwood, Herts, all of United Kingdom

[73] Assignee: Imperial College of Science, Technology and Medicine, London, United Kingdom

[21] Appl. No.: 08/945,843

[22] PCT Filed: May 10, 1996

[86] PCT No.: PCT/GB96/01121

§ 371 Date: Apr. 23, 1998

§ 102(e) Date: Apr. 23, 1998

[87] PCT Pub. No.: WO96/35945

PCT Pub. Date: Nov. 14, 1996

[30] Foreign Application Priority Data

May 10, 1995 [GB] United Kingdom .................. 9509410

[51] Int. Cl.[7] .................................................. G01N 21/33
[52] U.S. Cl. ................. 204/612; 382/128; 422/82.05
[58] Field of Search ............................... 204/612, 450, 204/456, 457, 466, 672; 422/82.05, 82.06, 82.09; 382/128; 436/164, 172

[56] References Cited

U.S. PATENT DOCUMENTS

| | | | |
|---|---|---|---|
| 3,824,680 | 7/1974 | Kozlov et al. | 29/592 |
| 4,389,670 | 6/1983 | Davidson et al. | 358/111 |
| 4,438,030 | 3/1984 | Ganfield et al. | 260/112.5 |
| 4,539,297 | 9/1985 | Clarke et al. | 436/164 |
| 4,592,089 | 5/1986 | Hartman . | |
| 4,666,578 | 5/1987 | Yamamota . | |
| 4,671,853 | 6/1987 | Takayama | 156/659.1 |
| 4,774,175 | 9/1988 | Chang et al. | 435/5 |
| 4,891,521 | 1/1990 | Danos | 250/370.09 |
| 4,892,409 | 1/1990 | Smith | 356/414 |

FOREIGN PATENT DOCUMENTS

| | | |
|---|---|---|
| 0 386 925 A1 | 9/1990 | European Pat. Off. . |
| 0 497 468 A2 | 8/1992 | European Pat. Off. . |
| 57-20655 | 2/1982 | Japan . |
| 90 067349 | 11/1991 | Japan . |
| 92 01 42975 | 12/1993 | Japan . |
| 2 259 980 | 3/1993 | United Kingdom . |
| WO 94/01581 | 1/1994 | WIPO . |
| WO 94/12871 | 6/1994 | WIPO . |
| WO 95/10041 | 4/1995 | WIPO . |

OTHER PUBLICATIONS

Marchywka, Mike; Binari, Steven C.; Pehrsson, Pehr E.; Moses, Daniel, "Development of Integrating Radiation Imagers with Diamond MIS Devices." Proc. SPIE–Int. Soc. Opt. Eng. (Jan. 1994), 2151 (Diamond–Film Semiconductors), 110–20.

Marchywka, Mike; Binari, Steven C.; Pehrsson, Pehr E.; Moses, Daniel, "Recent results in diamond UV detector research." Proc. SPIE–Int. Soc. Opt. Eng. (Jul. 1994), 2282(Ultraviolet Technolo), 20–30.

MacDonald, J.H.; Mahon, A. R.; Allers, L. A.; Hassard, J. F.; Mainwood, A.; Ott, R. J. "A CCD System for UV Imaging of Biomolecules." Nucl. Instrum. Methods Phys. Res., Sect. A (1997), 392(1–3), 227–232.

(List continued on next page.)

*Primary Examiner*—Jill Warden
*Attorney, Agent, or Firm*—Wallenstein & Wagner, Ltd.

[57] ABSTRACT

A method of imaging molecules of interest within a biological sample includes shining a UV light onto the sample and detecting the molecular UV absorption. Where the molecules of interest are themselves UV absorbers, the intrinsic absorption of those molecules may be used. If the molecules of interest are not good UV absorbers, UV-absorbing tag molecules may be used. The method may be used in molecular imaging devices of all types, and in DNA sequencers. A novel diamond-based detector is disclosed which is suitable for many applications.

15 Claims, 4 Drawing Sheets

U.S. PATENT DOCUMENTS

| | | | |
|---|---|---|---|
| 5,021,646 | 6/1991 | Weinberger et al. | 250/227 |
| 5,074,980 | 12/1991 | Vasta-Russell et al. | |
| 5,079,425 | 1/1992 | Imai et al. | 250/370.01 |
| 5,114,551 | 5/1992 | Hjerten et al. | |
| 5,141,609 | 8/1992 | Sweedler et al. | |
| 5,212,385 | 5/1993 | Jones | 250/370.01 |
| 5,214,288 | 5/1993 | Oka et al. | |
| 5,340,728 | 8/1994 | Grosz et al. | 435/91.2 |
| 5,348,658 | 9/1994 | Fuchs et al. | 210/656 |
| 5,432,071 | 7/1995 | Ichikawa et al. | 435/190 |
| 5,449,781 | 9/1995 | Varki et al. | 546/271 |
| 5,462,646 | 10/1995 | Sheih | 204/180.1 |

OTHER PUBLICATIONS

Mahon, A. R.; Allers, L.; Ott, R. J.; Hassard, J. F.; Mainwood, A. "Preliminary Results from CVD Diamond Detectors for Biomolecular Imaging." Nucl. Instrum. Methods Phys. Res., Sect. A (1997), 392(1–3), 274–280.

David A. McGregor, "Interactive Control of Pulsed Field Gel Electrophoresis via Real Time Monitoring," *Analytical Chemistry*, vol. 64, No. 1, Jan. 1, 1992, pp. 1–6, Washington, D.C., U.S..

J.L. Beckers, "Use of a Double–Detector System For the Masurement of Mobilities in Zone Electrophoresis" *Journal of Chromatography*, vol. 452, 1988, pp. 591–600.

MOLECULAR IMAGING

TECHNICAL FIELD

The present invention relates to the general fields of molecular imaging and genetic sequencing.

BACKGROUND OF THE INVENTION

Current methods of nucleic acid sequencing and mapping, and protein and tissue imaging, are based on radioactive, bio- and chemiluminescent emitters, photographic plates, and some electronic techniques. None of these have in practice been found to be entirely satisfactory.

Fluorescent imaging, radio labelling and bio- and chemiluminescent markers used with film and/or emulsion are expensive, very slow, limited and difficult to interface to computers. The techniques involved are difficult, and require hazardous handling and disposal procedures requiring substantial technical expertise. The materials used are often difficult and expensive to obtain, and have short shelf lives. Photographic imaging, which is frequently used, takes days or sometimes weeks or months to accomplish, and is limited by virtue of its small dynamic range and relatively poor linearity of response.

Of the electronic techniques, phosphor imaging/multiwire proportional chamber (MWPC) and the microchannelplate/MWPC approaches are unpopular with many molecular biologists because of their limited linearity and cost.

It may be helpful by way of background to set out in some detail the current state of the art in nucleic acid imaging. There are two separate methodologies which are currently in common use, details of which are set out below.

First, there are those involving the use of a photographic film to visualise chemiluminescent or radioactive labels and secondly, those using a light emitter, such as ethidium bromide, which chemically binds to nucleic acids and emits orange light under UV stimulation. The first imaging technology is usually used in nucleic acid sequencing. This process involves the chemical labelling of a component of the sequencing reaction, usually the primer, with a radioisotope or chemiluminescent marker, or tag. Subsequent to the sequencing reaction and electrophoresis, this tag is used to image the position of the nucleic acid bands by the exposure of normal photographic film to the dried electrophoresis gel. This is a lengthy process, taking from 24 to 72 hours, depending on the sequencing technique used. Many of the radioactive markers used in nucleic acid sequencing are extremely hazardous and introduce extra complications to the sequencing process therefore any imaging system which removes the necessity for these markers would be extremely advantageous.

The second technology, that of light emitters, is generally used for DNA restriction analysis and plasmid construction planning. This technique relies on the imaging of nucleic acids in simple agarose gels using the carcinogenic chemical ethidium bromide which emits orange light after UV stimulation to visualise the size and estimate the concentration of nucleic acid present. Ethidium bromide is a highly undesirable component of this technique with dangerous accumulative medical consequences. Its removal from the imaging technique would be very advantageous in every application of agarose gel analysis.

Nucleic acid sequencing, as opposed to spatial imaging, normally makes use of a rather different process. This process involves the chemical labelling of a component of the sequencing reaction, usually the primer, with a radio-isotope or bio or chemiluminescent marker, or tag. Subsequent to the sequencing reaction and electrophoresis, this tag is used to image the position of the nucleic acid bands by exposing photographic film to the dried electrophoresis gel. This is a lengthy process, taking from 24 to 72 hours, depending on the sequencing technique used.

DNA restriction enzyme analysis (DNA mapping) and vector construction is a fundamental aspect of molecular biology. These mapping techniques also rely on the photographic imaging of nucleic acids fragments in simple agarose gels using ethidium bromide. This marker emits orange light after UV stimulation, to visualise size and estimate concentration of nucleic acids. Ethidium bromide is an undesirable component of this technique with dangerous cumulative carcinogenic consequences. Its removal from the imaging technique would be very advantageous in every such application of agarose gel analysis.

The imaging of peptides and proteins is often the end destination of many genetic engineering processes. However, it also forms a huge portion of general biological, biochemical and medical research. Indeed, it is hard to think of a bioscience area that is not dependent, at least in some way, on protein analysis. The analysis is again normally based on electrophoretic techniques, being dependent on the addition of a marker. Generally these are radioactive although chemiluminescence and specialised chemical stains are also used.

The field of tissue imaging is hugely important in the areas of drug development, and medical and molecular diagnostics. Traditionally, β-emitting markers may be used to image the distribution of a drug within a tissue sample. This process typically takes weeks or even months, and requires the use of potentially hazardous substances.

It will be understood that all of the present methods mentioned above require the use of either radioisotopes or other hazardous substances in addition, at least some of the techniques listed require the use of expensive and inconvenient electrophoresis gels. To summarise, the major problems are as follows:

1. Training.

Health & Safety standards require all workers in contact with any form of radioactivity to have extensive training in the handling, use and disposal of radioactivity.

2. Use.

The incorporation of radioactivity into a system is often a complex and time-consuming process. The worker must take extreme precautions, for example with the isotope $^{32}P$, which is commonly used in DNA sequencing, has to be shielded from the worker by perspex, which makes an already complex experiment much harder. Subsequent to the initial experiment, the further manipulation of the already fragile electrophoresis gel is complicated by the radioactivity present. Radioactivity can be replaced by chemi- or bio-luminescent imagers, but these, and while these are safer they are still complicated to use.

3. Time.

All these imaging systems rely on the use of autoradiography to visualize the nucleic acids or proteins. This is achieved by drying the gel onto a piece of filter paper and exposing it to a piece of photographic film. The film must be exposed for anything between 24 hrs to 3 months. Therefore it can take from days to months to even see if the experiment worked. This is a major problem in molecular biology and increases the length of research projects significantly.

4. Expense.

The various components of these experiments are expensive. Radioactivity has a limited shelf-life because of its natural decay, and it is also expensive, with $^{35}$S costing about £250 for 20 sequencing reactions. The film used is also very expensive as some of it measures 35×45 cm.

5. Disposal.

These processes generate large volumes of solid and liquid waste, all of which must be disposed of legally and responsibly. This is also very expensive and troublesome.

SUMMARY OF THE INVENTION

According to a first aspect of the present invention there is provided a method of imaging molecules within a biological sample comprising shining a UV light onto the sample, and detecting the position of molecules of a selected class by the molecular UV absorption of molecules of that class.

According to a second aspect of the present invention there is provided a molecular imaging device for imaging molecules with a biological sample, comprising a UV light source arranged to shine onto a sample to be investigated and a UV detector arranged to detect the position of molecules of a selected class by the molecular UV absorption of molecules of that class.

According to yet a further aspect of the present invention there is provided an electrophoresis apparatus comprising an electrophoresis material onto which samples to be analysed are loaded, means for applying a potential difference along the material thereby causing the samples to move (migrate or drift) along the material, and a fixed detector located part way along the material and arranged to detect molecules of a selected class as they move past the detector.

According to yet a further aspect there is provided an electrophoresis apparatus comprising an electrophoresis material onto which samples to be analysed are loaded, means for applying a potential difference along the material thereby causing the samples to move (migrate or drift) along the material, a light source arranged to shine onto the material and a detector arranged to detect the position of molecules of a selected class by the molecular light absorption of molecules of that class.

In the preferred method of the present invention, molecules are imaged by detecting their intrinsic absorption of UV light. In this aspect of the invention, we use the intrinsic image of the molecule itself, whether it be a nucleic acid fragment, a protein, or indeed a polypeptide chain. The image comes from the absorption of that molecule, using molecular UV absorption spectrometry, in contrast to the well known technique of optical spectrometry. The key advantage is the lack of a tag.

This has many important consequences. Perhaps the most obvious is that no hazardous tag is no longer needed, whether it be radioactive or a well known carcinogen like ethidium bromide. Another issue is that, for sequencing reactions, the lack of the tag removes one of the major constraints on the number of bases that can be sequenced: that is, the amount of radioactivity that can be incorporated within the sample.

Preferably, the molecules of interest are directly imaged by detecting their absorption by imaging the nucleic acid, protein or tissue map onto a diamond detector. This may be accomplished by illuminating the object to be imaged—whether it be nucleic acids, proteins or tissue, with constant brightness UW light from either a broad spectrum device like Helium discharge tube, or a monochromatic laser like an excimer laser at 196 nm. We observe the different amounts of light reaching a detector placed behind the object being imaged. In the case of two or three dimensional imaging, the shadow is imaged simultaneously, and the object thereby identified. This requires a two-dimensional detector, like a pixel device or a pixellated ridge device.

In the superior case of the directional laser, we can scan the object to be identified onto a one dimensional detector, either planar (with strip electrodes) or ridged, and build up a two dimensional image. The latter case is superior in an additional way: by making two (or more) scans with non-parallel laser beams, a stereoscopic image can be made, allowing 3D reconstruction.

When the invention is applied to nucleic acid manipulation and quantitation, the technology will allow a quantitative differentiation between transmitted and absorbed energy. The quantitation of DNA under these conditions has important applications in the construction of expression vectors that are used to produce specialised proteins used in therapeutics.

When the present invention is applied to the imaging of peptides and proteins, the same equipment may be used as that used to image DNA restriction enzyme maps. The speed of imaging provided by the present invention offers significant advantages over existing techniques, some of which can take up to three months.

This idea is based on the absorption by proteins of UV light at <230 nm, also an optimal range for nucleic acids. Thus the same detector could image both types of molecules. An added bonus of the feature is that lipids, carbohydrates and other small macromolecules absorb UV poorly if at all in this range, thus allowing an intrinsic filtering of biological noise on the image.

This spectral response is ideally matched to that of diamond, which turns on at 224 nm, and is extremely insensitive to light of greater wavelengths or lower energy. This is a very powerful attribute for a detector to have. A typical wavelength range for a diamond detector is about 180–224 nm, but since the lower limit is imposed more by the materials and/or source than the detector medium, lower wavelength detection may not be excluded in all circumstances. For certain applications, silicon detectors could be used (detection range 190–300 nm). Photomultipliers might also be used.

In its application to tissue imaging, two-dimensional images may be built up using a pixelated detector, or a strip in which the source is scanned orthogonally to the strips. In the preferred embodiment of the invention, a diamond detector is used, and two-dimensional images are built up by pixellating the diamond or scanning the UV source orthogonally to the strips. Most usefully, three dimensional stereoscopic images can be built up by the addition of images from non-parallel lasers imaged on the same detector. In this case, we propose to strobe alternately the lasers, with the detector read out with the parallax shifts determining the three-dimensional structure. A highly resolved three-dimensional image will allow details on the tissue structure to be derived. This will greatly cut down development time for a new drug and hence reduce the overall cost.

In one preferred embodiment, the invention extends to an electrophoresis apparatus, for example to a DNA sequencer. The apparatus preferably monitors qualitatively the changes in a signal from a source as bands of nucleic acids passed between the source and the detector on an electrophoresis gel. As the bands pass the detector, they may be digitised directly to a data base.

The apparatus may further incorporate the concept of using inert reusable solid phase for the electrophoresis. For a DNA sequencer, the solid phase may be coated or otherwise supported on a quartz substrate (for example a tube), there preferably being four separate tubes for the four bases.

To summarise, the following are the primary advantages of the present invention, or subsidiary aspects of the present invention:

1. Training.

The removal of radioactivity from the systems obviates the need for Health & Safety training.

2. Use.

The removal of radioactivity or any other extrinsic imaging component from the experimental process dramatically increases the efficiency and speed of those reactions. The labelling step (where the radioactive marker is added to the reaction) is often complicated, and its failure cannot be perceived until the end of the experiment.

3. Time.

The ability to image the results of, for example, a sequencing gel in minutes rather than hours is expected to lead to a dramatic increase in the efficiency of large scale sequencing operations such as the Human Genome Project. It would also allow the faster discovery of problems within the reaction—a lot of time is lost in molecular biology due to the time it can take to realise that an experiment has not gone according to plan.

4. Expense.

The application of hardware based on this technology would lead to a massive release of funds from any research groups consumables budget. Following the initial equipment costs, many molecular biology groups could expect to see their radioactivity and film requirements drop substantially.

5. Disposal.

Environmentally, the benefits of the technology are immense. The total removal of radioactivity from the system of course eliminates the need for its disposal.

According to another aspect of the invention there is provided a method of identifying individual substances within a mixture of substances comprising:

(a) causing the mixture to travel past a spaced plurality of detectors, each detector $I_k$ being arranged to produce a signal $S_k$ representative of a characteristic of the mixture as it passes the detector $I_k$;

(b) repeatedly measuring the signal $S_k(t)$ at each detector $I_k$ at a plurality of times t =$t_1$, $t_2$, $t_3$ . . . ;

(c) grouping the signals $S_k(t)$ by nominal velocity $V_k(t)$, the velocity needed for a substance within the travelling mixture to reach the detector $I_k$ at time t, and (d) identifying individual substances within the mixture according to peaks within the collection of grouped signals.

According to another aspect there is provided a method of identifying individual substances within a mixture of substances comprising:

(a) causing the mixture to travel past a spaced plurality of detectors, each detector $I_k$ being arranged to produce a signal $S_k$ representative of a characteristic of the mixture as it passes the detector $I_k$;

(b) repeatedly measuring the signal $S_k(t)$ at each detector $I_k$ at a plurality of times t =$t_1$, $t_2$l $t_3$ . . . ;

(c) grouping the signals $S_k(t)$ in velocity space; and (d) identifying individual substances within the mixture according to peaks within the grouped signals in velocity space.

By transforming into velocity space and integrating over time the individual substances (for example biomolecules) may be rapidly identified as individual spikes or peaks in velocity space. The size and/or width of each peak may be used to obtain a measure of the amount of each individual substance.

The use of the word "substance" has to be read extremely broadly since the method in its most general form may be applicable to many applications other than the recognition and identification of biomolecules. The same method might for example be used to identify the flow of individual substances down a common pipeline, and it may also find application with individual discrete objects such as in the analysis of traffic flows.

In transforming to velocity space, a calculation may be undertaken of the velocity that is needed for a substance within the travelling mixture to reach a given detector $I_k$ at the time t at which the signal from that detector has been recorded. This nominal velocity may be calculated as $Z_k$ over t where $Z_k$ is the distance from an origin to the detector $I_k$ and t is the time elapsed. There may however be other methods of determining nominal velocities, for example measuring the time taken for a known substance to move between one detector and the next. It would also be possible to determine velocity by identifying a particular sequence of bands at one detector and measuring how long it takes that sequence of bands to move, on average, to the next detector. In that way, an individual band within the sequence may be identified and accurately timed at two separate detectors, with the velocity then being calculated from a knowledge of the distance between the detectors.

BRIEF DESCRIPTION OF THE DRAWINGS

The invention may be carried into practice in a number of ways and several specific embodiments will now be described, by way of example, with reference to the drawings, in which.

DETAILED DESCRIPTION OF THE PREFERRED EMBODIMENTS

Figure 5:
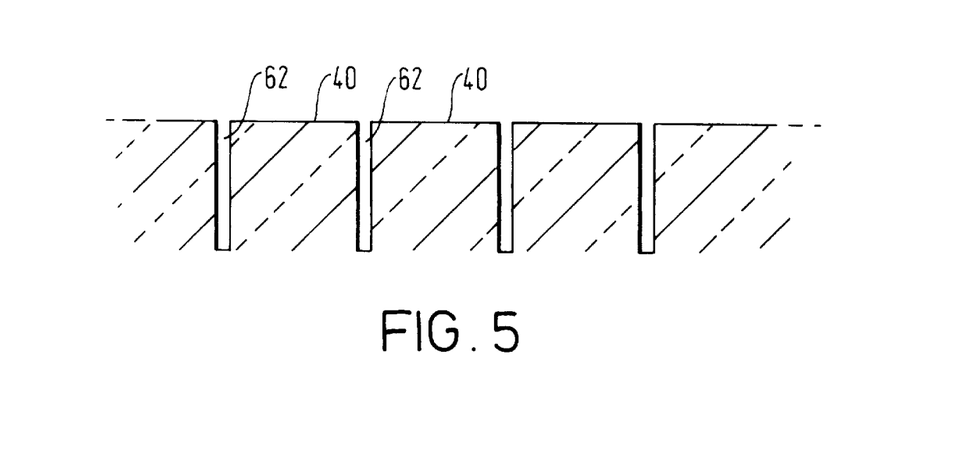
FIG. 5 shows yet a further embodiment of a detector suitable for use with the method and apparatus of the present invention.
Figure 6:
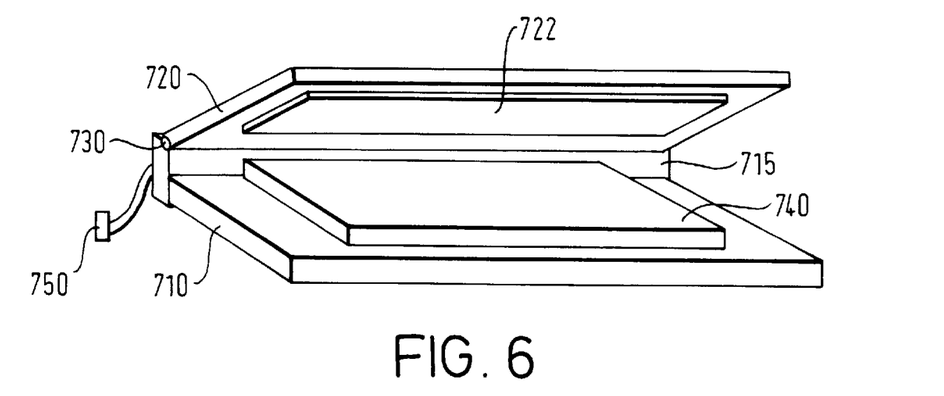
FIG. 6 shows a molecular imaging device comprising an embodiment of the present invention.
Figure 7:
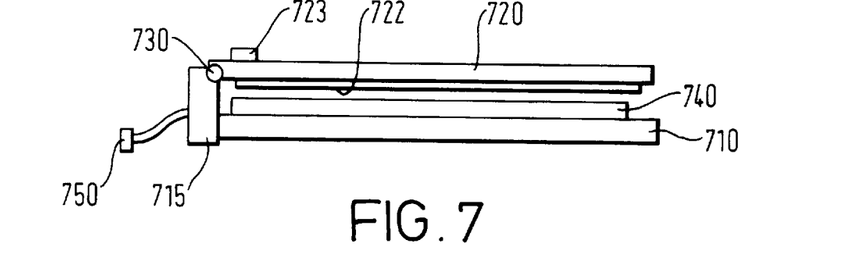
FIG. 7 shows a side view of the imaging device of FIG. 6.

Referring first to FIGS. 6 and 7, there is shown a molecular imaging device comprising a preferred embodiment of one form of the present invention. The device shown in FIGS. 6 and 7 is primarily a nucleic acid/protein imager, and in its most straightforward form it comprises a generally flat base portion 710, a body portion 715 secured along one edge of the base portion and a lid 720 which is pivotally secured to the body portion 715 by means of an elongate hinge 730. Between the lid and the base is an electrophoretic gel mount 740. The base portion 710 incorporates a scanning UV detector assembly, preferably although not necessarily having a detector of the form that will be described later with reference to FIGS. 1 to 5.

To use the imager, the lid 720 is first raised, and a sample (not shown) to be imaged is placed on the mount 740. The sample may include, amongst other things, an electrophoresis gel containing molecular samples that have been separated in a conventional way using an electric field, a thin section through biological tissue, or a monolayer of cells that has been grown on the surface of a suitable flat mount. Once the sample has been placed in position, the lid 720 is closed, and an ultra-violet light box 722 attached to the underside of the lid is switched on. This bathes the samples in ultra-violet light, with the amount of UV absorption being detected by the detector assembly with the base portion as the detector scans transversely across the sample. The detected pattern of absorption across the surface of the sample is digitized, and is transferred via a data port 750 to an external computer (not shown) running a suitable graphics program.

The light box 722 may incorporate any suitable ultra-violet source, such as a deuterium lamp. A switch 723 provides the capability for the user to switch between UV wavelengths, so that both nucleic acids and proteins may easily be imaged.

In an alternative arrangement, the UV source could be mounted to a transverse scanning assembly (not shown) secured to the lid 720. In that arrangement, the UV source would scan across the sample while the detector, within the base portion 710, could remain stationary. It would also be possible for both the UV source and the detector to be mounted to scanning assemblies, both assemblies scanning across the gel at the same speed. In either the preferred or in the alternative arrangement, a tunable laser may be used as the light source. In one particular arrangement, a pair of lasers may be provided, or alternatively a twin beam laser, in which the beams are aimed at the sample from different directions. This provides the possibility of carrying out stereoscopic imaging, and by the use of a suitable beam scanning mechanism providing three-dimensional as well as two-dimensional imaging 875. Such imaging may be extremely useful as it enables researchers to investigate the distribution of nucleic acids and/or proteins within the thickness of the sample being studied. One would, for example, be able to detect the distribution of nucleic acids and proteins within individual cells. With the possible use of differentially absorbing tags, one can detect how drugs accumulate within a cell. One can also detect how viruses build up in cells.

The advantage of using the preferred diamond detector, to be described later with reference to FIGS. 1 to 5, is that the detector is naturally rather insensitive to absorption occurring in biological structures which are of no particular interest, such as lipids and carbohydrates. The appropriate resolution may be determined, by simple experiment, according to the particular application. It is expected that for the detection of nucleic acids and proteins at reasonable resolution one would use a ridge size (width) of between about 5 and 200 $\mu$m.

Figure 8:
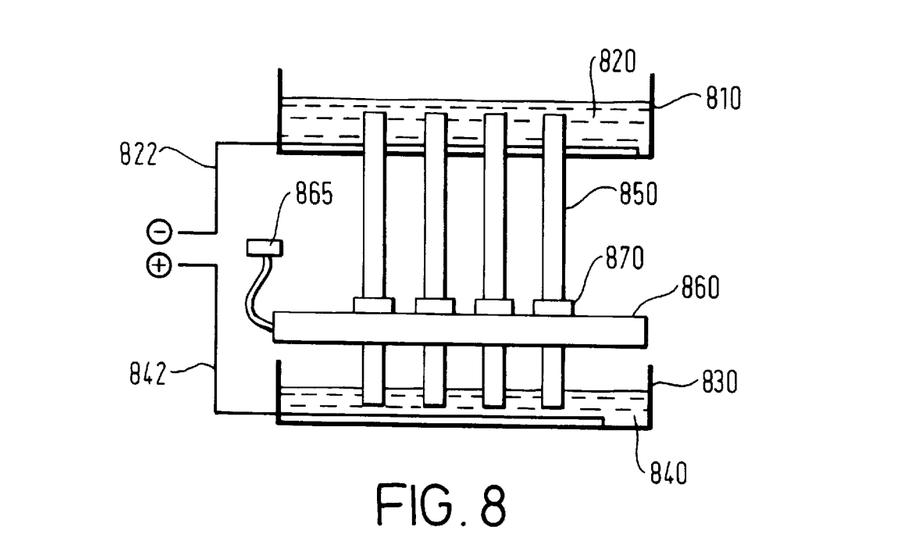
FIG. 8 shows, schematically, an automated DNA sequencer comprising another embodiment of the present invention.
Figure 9:
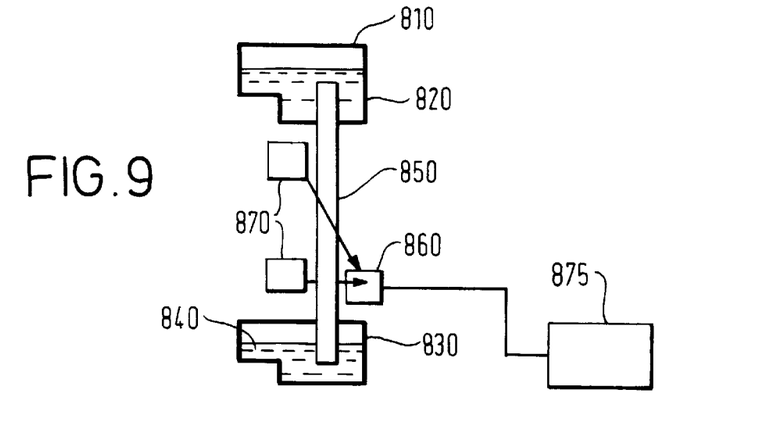
FIG. 9 is a schematic section through the sequencer shown in FIG. 8.

Reference will now be made to FIGS. 8 and 9 which show schematically an automated DNA sequencer according to an embodiment of a further form of the present invention.

FIGS. 8 and 9 show one sub-unit of the proposed sequencing machine. The machine as a whole comprises four or five such sub-units. Each sub-unit comprises a top buffer reservoir 810 containing buffering solution 820; a lower reservoir containing buffering solution 840; a UV source 870 or a plurality of such sources; a UV detector 860 linked to a standard readout 865; a cathode 822 linked to the buffer solution 820; and an anode 842 linked to the buffer solution 840. The device also includes four solid phase matrix tubes, 850 which extend between the upper and lower reservoirs.

Both the upper and lower reservoirs 810,830 may be constructed of a clear plastics material, and contain simple buffer solutions 820,840 to prevent the excessive build up of acidity in the system. The solid phase matrix tubes 850 contact the buffer solution 820 at the top and the buffer solution 840 at the bottom.

The light source 870 comprises a UV lamp or a deuterium or discharge lamp. Alternatively, it could comprise a laser capable of operating in the range between 220 nm and 180 nm, or even a diode.

The detector 860 comprises any suitable optical detector, matched to the wavelength of the light source 870. The detector preferably comprises a diamond ridge detector, as will be described in more detail below with reference to FIGS. 1 to 5. The widths of the ridges may lie between 5 and 200 $\mu$m depending upon the wavelengths to be detected and the resolution required. The narrowness of the ridges and the fact that substantially planar illumination is used allows for great precision and resolution.

The detector 860 is linked to appropriate electronics which provide a digital readout at an output 865. A standard readout such as Labview (™), inputting directly into a suitable database processor such as MacVector (™) or MacDNAsys (™).

The solid phase matrix tubes 850 comprise four quartz tubes containing a suitable solid phase material. Suitable materials include silicon based pre-existing gel matrices such as the Sephadex (™) group. The solid phase is relatively UV transparent, and is also reusable. The length of the tubes is dependent upon the exact nature of the solid phase chosen, but will typically be no more than 15 to 20 $\mu$m.

In use, a voltage is applied between the anode and the cathode to produce a potential difference along the length of the solid phase matrix tubes 850. The four individual reactions to be detected are loaded, each onto their separate column, and electrophoresised to the anode. As the bands pass between the source 870 and the detector 860, a simple qualitative image of each band is digitised to a database. The resultant digital information may either be read out in real time, or it may be stored within the detection system electronics, until the electrophoresis is complete. All the information may then be read out at once.

After the sequencing mixture has been run through the column, all traces of the DNA can be removed by continuous exposure to an electric field and a buffer solution. After thorough washing, the solid phase may then be reused.

It should be noted that the simplicity of operation of the present device, and the reusability of the solid phase, follows at least in part from the fact that radioactive tagging is no longer required.

It will be appreciated, of course, that the invention in its most general form is not restricted to the specific features described above. Suitable equivalent devices may easily be constructed by a skilled person in the art, the exact details of those structures depending on the specific area of interest. Specific areas in which the device and method of the present invention may find application include tissue imaging, for example drug targeting, performance and cellular diagnostics; nucleic acid interrogation and mapping, including sequencing, restriction enzyme mapping, quantitation, High Pressure Liquid Chromatography (HPLC) and oligonucleotide purification; and protein imaging, including peptide analysis and monitoring of nucleic acid manipulation and medical diagnostics.

For suitable applications, a UV sensor such as is described below with reference to FIGS. 1 to 5 may be used. Such applications are likely to be those in which imaging can be achieved in the approximate range 220 to 190 nm. It is not essential, however, to use a ridged topology, such as is specifically described and, for certain applications, planar diamond detectors would be entirely adequate. The advantage of a diamond detector is its almost total lack of noise, its excellent quantum efficiency, and its linearity.

In regions which are not suitable for use with diamond detectors, such as for example the region 220 to 290 nm (where DNA absorbs), non-diamond semiconductors may be used. Suitable detectors would include UV enhanced silicon detectors and photomultipliers.

The preferred embodiments of the present invention may either make use of the intrinsic absorption properties of molecules, when exposed to light, or alternatively may make use of the absorption properties of tags attached to the molecules of interest.

Specialised molecular absorbers with differential molecular attachment may be used to improve sensitivity. Such absorbers may be non-toxic.

In some embodiments of the invention, stereo UV lasers may be used to create three-dimensional images of complex structures in the object being scanned, by simple shadowing software techniques. Again, this could be achieved either using the intrinsic absorption properties of the molecules being investigated, or by using specialised molecular absorber tags.

Figure 1:
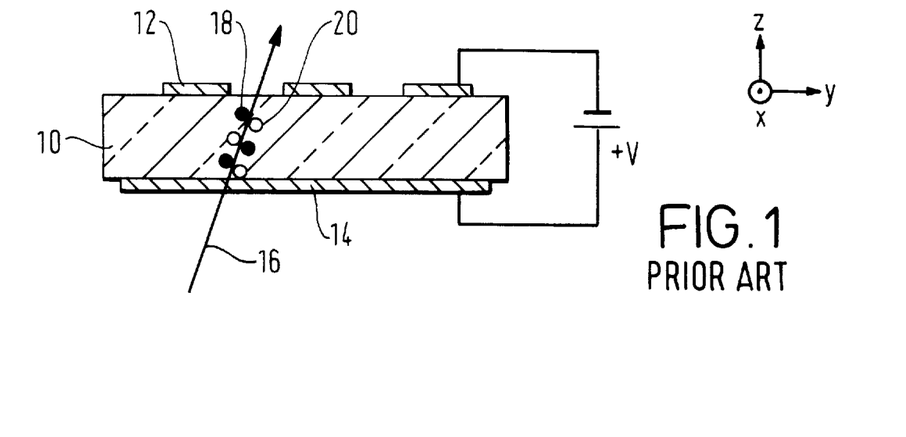
FIG. 1 shows a prior art detector.

A typical prior art detector of charged particles is shown in FIG. 1. The detector comprises a flat sheet of an insulating material such as diamond, having thin gold electrode coatings 12,14 on its upper and lower surfaces. The upper electrode coating 12 comprises a plurality of parallel readout strips which are aligned in a direction perpendicular to the plane of the paper in the Figure, and the lower electrode coating 14 comprises a further plurality of readout strips aligned in a direction parallel with the plane of the paper. A large potential difference V is maintained between the electrode coatings. Either the top or bottom electrode may be continuous, and the strips may have alternate polarity.

A charged particle following a path 16 through the diamond produces electron-hole pairs 18,20, which separate under the influence of the electric field and induce a charge on the readout strips. The energy of the particle can be determined by the amount of charge which is collected, and its position by the intersection of the upper and lower strips receiving the largest induced charges.

A preferred detector, suitable for use with the method and apparatus of the present invention, will now be described in detail, with particular reference to FIGS. 2 and 3. It is a diamond detector and comprises a diamond substrate 30 having, on one surface, a plurality of parallel etched diamond ridges 40. On one side of each ridge there is a positive readout electrode 50, and on the other side a negative electrode 60. These are preferably conductors, but could instead be of a high-conductivity doped semi conductor material.

In use, the detector is positioned so that the substrate lies substantially normal to a particle or radiation beam 70 to be detected. An individual particle passing into one of the ridges creates ionised carriers, which rapidly drift to the electrodes 50,60 by virtue of the large potential difference which is maintained between them. Charge is thereby induced on the electrodes, this charge being read off by readout devices (not shown) at the ends of the ridges.

The substrate and the ridges are preferably of diamond, which may either be natural or artificially grown. The ridges may either be grown, with the substrate, or they may be etched (for example with an eximer laser). The electrodes 50,60 may be of any material or combination of materials (for example titanium, vanadium, chromium and/or gold) which form an ohmic contact to the diamond surface with appropriate processing (for example ablation, ion implantation or annealing). Standard deposition techniques may be used to apply the metal as a thin coating to the sides of the ridges. Typically, the device may be made by etching the ridges, depositing the material, and then polishing the top surface.

Figure 2:
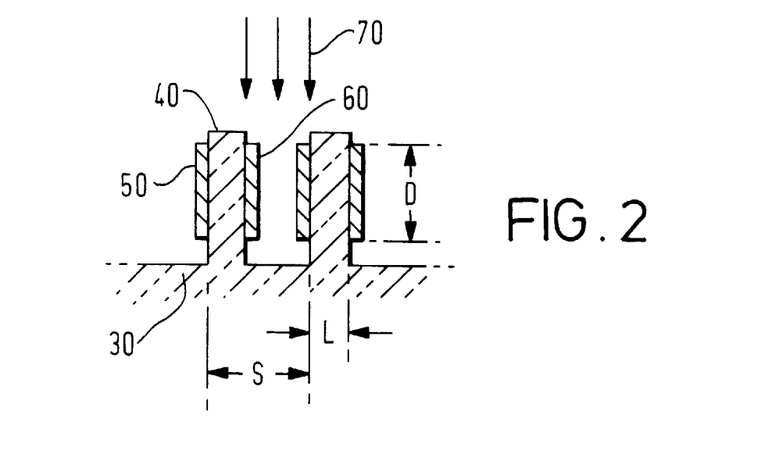
FIG. 2 is a cross-section through a detector suitable for use with the method and apparatus of the present invention.
Figure 3:
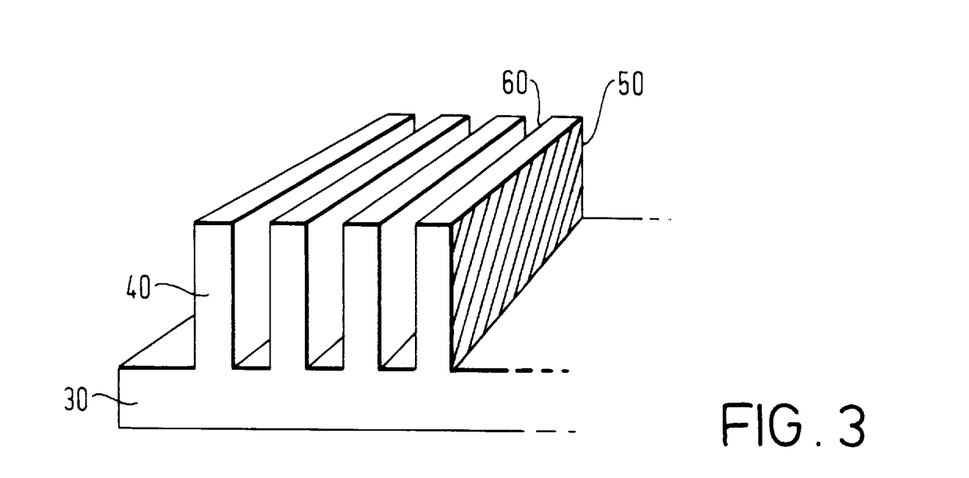
FIG. 3 is a perspective view of the detector of FIG. 2.

It will be appreciated from FIG. 2 that the sensitivity of the device shown can be increased by making the value of D (or the height of the ridges) larger. The greater the height of the ridges, the larger the amount of material which a particle has to pass through, thereby increasing the ionisation within the device. The height of the ridge will normally be matched to the expected penetration depth of the particles or photons to be detected. The readout speed and efficiency is determined by the width L of each of the ridges. Depending upon the particular application, the value of L may be as little as a few micrometers, or a larger value up to about 200 $\mu$m, and the value of D 10 $\mu$m or more. The signal-to-noise ratio is large, as there is negligible cross-talk between signals emanating from individual ridges. A typical substrate depth is around 100 $\mu$m, sufficiently thick to support the ridges and to be free-standing without requiring an additional supporting base. Preferably, the device makes use of relatively poor quality diamond, having a recombination length of perhaps 6 $\mu$m or so.

The impedance of the readout devices (not shown) at the end of the ridges is preferably matched with the impedance of the electrodes 50,60, thereby increasing readout speed and reducing signal losses.

There are a number of ways in which a potential difference may be applied between the electrodes 50,60 shown in FIG. 2. In its simplest form, a voltage source may simply be connected between the two electrodes. Alternatively, the electrodes may be coupled to a resistor chain (not shown), the potential difference between the electrodes thereby being defined by the potential drop across the corresponding resistor.

Figure 4A:
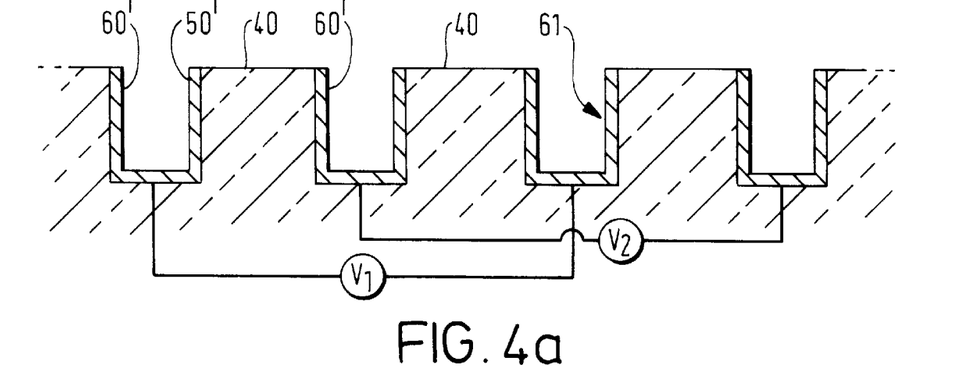
FIG. 4a shows another embodiment, the electrodes being connected in a bipolar voltage configuration.

Another embodiment is shown in FIG. 4, in which the electrodes are formed over the base and the sides of the space between the diamond ridges 40. This means, effectively, that each electrode 50' on the left side of a ridge 40 is electrically coupled with a corresponding electrode 60' on the right hand side of the next ridge in the sequence so that they together form a single U-shaped electrode 61. In the embodiment of FIG. 4a, first alternate pairs of U-shaped electrodes 6; are coupled via a first voltage source $V_1$, and second alternate pairs are coupled by a second voltage source $V_2$. Such a bipolar voltage configuration ensures that there is always a constant potential difference $V_1$–$V_2$ across each of the ridges 40.

Figure 4B:
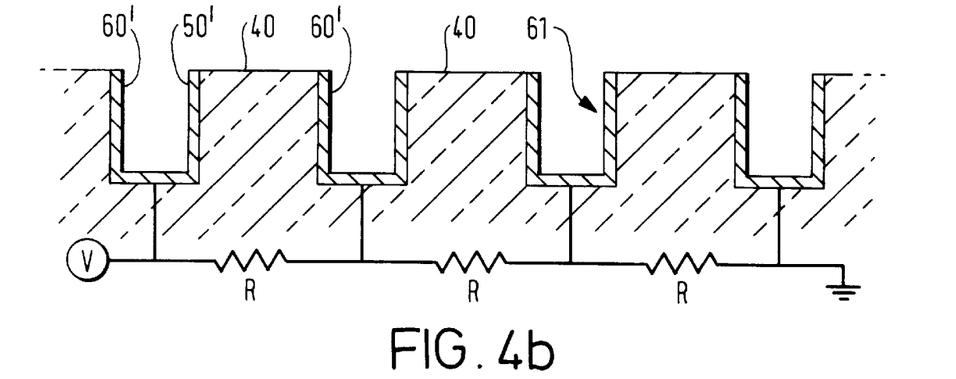
FIG. 4b shows the embodiment of FIG. 4a, the electrodes being connected in a resistor chain configuration.

An alternative method of applying voltages to the U-shaped electrodes 61 is shown in FIG. 4b. Here, a resistor chain is used to drop an input voltage V across a plurality of series resistors R. The voltage across each ridge 40 may be chosen by selecting appropriate values for V and R.

It will be understood, of course, that a similar bipolar voltage configuration or resistor chain voltage configuration may be used in conjunction with the embodiment of FIG. 2.

A typical potential difference across the ridge 40 may be in the region of 1 volt per $\mu$m. Substantially higher voltages could be used, if desired (since diamond has a very high breakdown potential), but there is generally no need for high potential differences since at greater voltages the carrier speed rapidly saturates.

In a further embodiment (not shown) a further parallel set of ridges, orthogonal to the first set, is provided on the lower surface of the substrate 30. These two perpendicular sets of ridges allow accurate x-y positioning of each detected particle.

The spaces between the ridges may be filled with a plastics material, or other absorber, thereby improving the capability of the detector to detect neutral particles.

Yet a further embodiment is shown in FIG. 5. Here, the spaces between the ridges 40 have become extremely narrow, and they each contain a separate electrode 62. Such an embodiment is, in many circumstances, preferred since the narrowness of the gaps between the ridges 40 produces only a small acceptance loss compared with the embodiments of FIGS. 2,3 and 4. The width of the gap, and hence the width of the electrode 62, may depend primarily on how narrow a slot can be cut into the diamond substrate. The electrodes 62 may be coupled together in any convenient manner so as to produce a suitable potential difference across the ridges 40, for example using the approach of FIG. 4*a* or of FIG. 4*b*.

The detection of high energy electromagnetic radiation, such as gamma rays, may be improved by adding a showering layer (not shown) on top of the ridges. An incoming photon first strikes the showering layer, and the resulting shower then penetrates into one of the ridges below, providing a signal which be detected.

The ionizing radiation detector described above can provide extremely rapid charge readout, probably within 35 ps and certainly within 50 ps. These readout speeds cannot currently be achieved for any single pulse detector of comparable sensitivity and positional accuracy.

We turn now to a discussion of the way in which the above apparatus may be used in practice to identify individual molecules within a mixture.

Figure 10:
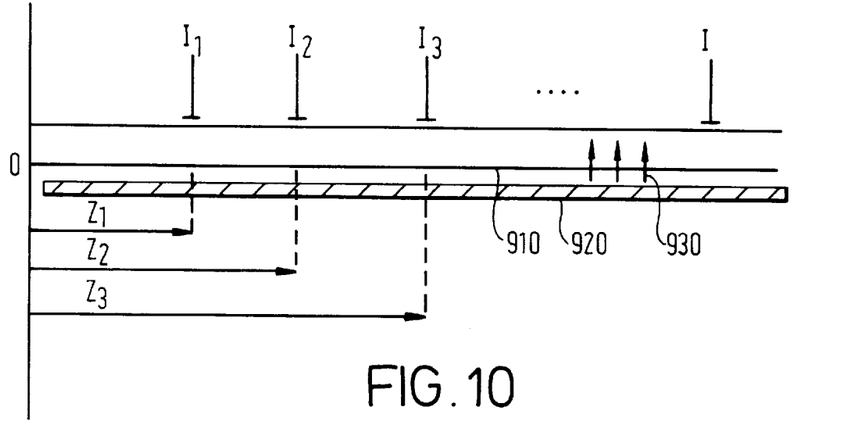
FIG. 10 schematically illustrates the preferred embodiment of isolating biomolecules.

FIG. 10 illustrates the arrangement schematically. On one side of an elongate substrate 910 along with the molecules will move is a UV lamp 920 while on the other side there is a series of spaced UV detectors $I_1, I_2, I_3, \ldots I_n$. As has previously been discussed, sequencing is achieved by detecting the passage of bands of biomolecules in front the detector elements. Since the biomolecules absorb UV light in the region of interest, the passage of any band in front of a detector induces a drop in the nominally DC current which is caused by the constant illumination 930 of that detector element by the UW light source 920. The drop in current is measured and tagged, and treated as an individual signal which may be related to a given biomolecule band. Nominally, in an electrophoretic gel, the velocity of a given band is inversely proportional to the root of the mass of the sequence of nucleic acid in the band; the charge of the sequence is decoupled from its length by frictional retardation forces which impose a "terminal velocity" caused by those forces being proportional to the length.

In order to identify the individual molecules the system automatically collects a sequence of signals $S_k(t)$ for the array of detectors $S_k$ at times $t = t_1, t_2, t_3 \ldots$ Now, since the position of each detector element is known and the elapsed time is also known, it is possible to calculate the velocity that a particular molecule would have needed to reach a particular detector in that given elapsed time. If we assume, for example, that the elapsed time is measured from $t_0=0$, and that the detector $I_k$ is a distance $Z_k$ from the origin O, we can calculate the nominal velocity $V_k(t)$ by means of the expression $Z_k/t$.

Each signal $S_k(t)$ is then added to an appropriate bin in a weighted running histogram which is grouped by nominal velocity. The individual signals may be added to the appropriate bin in any convenient manner, but in the preferred embodiment a weight w is added to the bin for each signal, the weight being proportional to the signal size $S_k(t)$. A corresponding graph or histogram of the weights plotted in velocity space is shown in FIG. 11.

Figure 11:
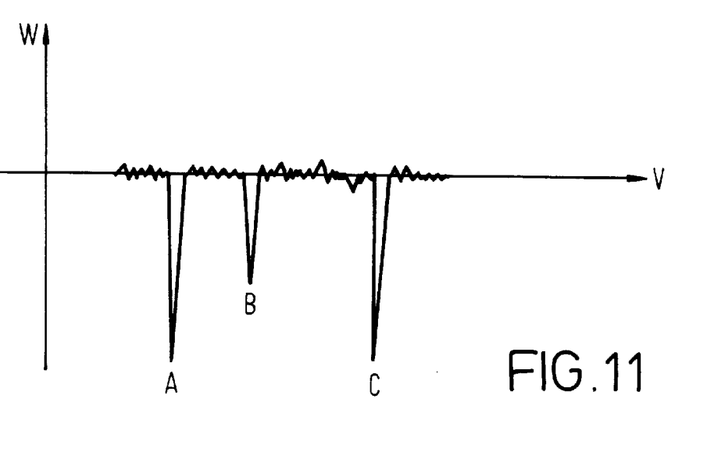
FIG. 11 shows the results of the preferred analysis as a graph in velocity-space.

Since each different biomolecule to be detected is of a different length, it will travel at a different velocity, and hence will appear in a different place in the FIG. 11 histogram. Individual molecules appear as separate spikes or peaks in the histogram; in the examples shown molecules A, B and C have been detected.

In one possible arrangement, the signals $S_k$ may be repeatedly collected for times $t_1, t_2, t_3$ and so on. Once all the data have been collected they may then be plotted and analysed as shown in FIG. 11. In an alternative and preferred arrangement, however, the data are grouped as they are being collected. The advantage of such an arrangement is that a graph such as is shown in FIG. 11 may be plotted, for example on a computer screen, and may be updated in real time. As the data collection proceeds the spikes representative of detected molecules gradually become more distinct.

It will be understood that the time period between successive samplings of the detectors may be chosen according to the application. In the preferred embodiment, the sampling occurs every one hundred milliseconds, but for other applications the period might be as small as a few microseconds or as large as several minutes or even hours. Provided that the readout electronics can handle the flow of data, there is no real price to pay for going to shorter and shorter times. In addition, there is no need for the time periods to be contiguous, although in practice contiguous periods of measurement are likely to be more convenient, particularly with the present application in which the period is defined by the drift velocity, the size of the bands and certain other factors.

It will be recalled that the signal $S_k$ at each detector $I_k$ is representative of the current offset from the nominal DC level which is present when there are no molecules in the path of the beam 930. Statistical fluctuations may take this signal either negative (that is above the average DC level) or positive (that is below the DC level). On average these will tend to cancel, and as more data are collected, the noise is gradually suppressed. By not trying to follow individual objects, but instead "blindly" summing the values in velocity space at each step, the objects are found automatically in a way which is natural, very quick, and which minimises noise. The hardware needed is very simple, and the software and analysis even more so. The hardware could for example be provided by the charging of a capacitative element by an amount proportional to the signal $S_k$.

A further advantage of the method is that not only is automatic background subtraction carried out, but the precision obtained is far greater than would be possible by the simple use of information from individual detector elements.

The information from the array $S_k$ as a whole provides far greater information and hence precision than could be obtained from a consideration of the detectors individually.

In addition, the method also allows quantification. By considering the height and width of each of the spikes in FIG. 11 one can determine with some accuracy how much of each detected substance was contained in the original mixture.

The use of an essentially planar light beam 930, and directional detectors, ensures that the molecules may be located extremely precisely as they pass the detectors. While it would of course be possible to use the method described with molecules that emit a signal to be detected, such as radioactivity or UV light, the precision is likely to be lower due to additional scattering and the fact that the concentration of molecules has to be larger to produce the same signal (since most of the emitted light or radioactivity is wasted as it is emitted in all directions). By using UV absorption to produce the signal, one can use very much smaller molecules so that they move faster and separate faster. This enables the reading time to be drastically cut to perhaps minutes rather than the conventional hours.

It will be appreciated that the method described may have applications other than the sequencing of biomolecules. Other applications in which such a technique might be of use include on-line process control, for example in tracking individual items in a supply pipe, or monitoring traffic flow. More generally, the method may be applied to assessing the distribution of items in a time-varying multi-dimensional density distribution. The general method allows one not only to identify individual substances within a mixture of substances, but also to calculate their proportions.

The invention claimed is:

1. A molecular imaging device for imaging molecules within a biological sample, comprising:
    a UV light source arranged to shine onto a sample to be investigated;
    a UV detector arranged to detect the position of molecules of a selected class by the molecular UV absorption of molecules of that class, wherein the detector comprises a single wafer of detector material, the wafer having a plurality of parallel sided grooves in a surface thereof thereby defining between the grooves and plurality of parallel sided detector elements, opposing sides of each element carrying opposing readout electrodes; and
    means for applying a potential difference between the opposing electrodes of each element to create an electric field across the element.

2. The molecular imaging device as defined in claim 1 further including a digitizer for digitizing the molecular positions, on detection, and for building up, as detection proceeds, a digital image of the molecular positions.

3. The molecular imaging device as defined in claim 1 wherein the detector determines the spatial distribution of molecules of the selected class within a sample.

4. The molecular imaging device as defined in claim 3 further including scanning means for scanning the detector with respect to the sample, of vice versa.

5. The molecular imaging device as defined in claim 1 wherein the detector is stationary with respect to the sample and is arranged to detect molecules of the said selected class as the molecules move on or within the sample past the detector.

6. The molecular imaging device as defined in claim 5 wherein the UV source is located opposite the detector.

7. The molecular imaging device as defined in claim 1 wherein the detector material comprises diamond.

8. The molecular imaging device as defined in claim 1 wherein the detector material comprises UV enhanced silicon.

9. The molecular imaging device as defined in claim 1 wherein the detector is pixellated for imaging in two dimensions.

10. The molecular imaging device as defined in claim 1 wherein the UV light source is arranged to shine onto the sample from two different directions, the device further including three-dimensional image reconstruction means for reconstructing the molecular image positions in three-dimensions based on differences in absorption between the two directions.

11. The molecular imaging device as defined in claim 10 wherein the light is arranged to shine in a first direction, followed by a second direction.

12. The molecular imaging device as defined in claim 1 wherein the light source is a UV laser.

13. The molecular imaging device as defined in claim 1 wherein the light source is a Deuterium lamp.

14. The molecular imaging device as defined in claim 1 wherein the light source is a Helium discharge tube.

15. The molecular imaging device as defined in claim 1 wherein the detector comprises a photomultiplier.

* * * * *